US007723035B2

(12) United States Patent
Croce et al.

(10) Patent No.: US 7,723,035 B2
(45) Date of Patent: May 25, 2010

(54) COMPOSITIONS AND METHODS FOR CANCER DIAGNOSIS AND THERAPY

(75) Inventors: Carlo Croce, Philadelphia, PA (US); George Calin, Philadelphia, PA (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 11/375,650

(22) Filed: Mar. 13, 2006

(65) Prior Publication Data

US 2006/0165659 A1 Jul. 27, 2006

Related U.S. Application Data

(63) Continuation of application No. 10/706,798, filed on Nov. 12, 2003, now abandoned.

(60) Provisional application No. 60/425,864, filed on Nov. 13, 2002, provisional application No. 60/469,464, filed on May 9, 2003.

(51) Int. Cl.
*C12Q 1/68* (2006.01)
*C07H 21/04* (2006.01)
*A61K 31/70* (2006.01)

(52) U.S. Cl. .......................................... 435/6; 536/24.1

(58) Field of Classification Search ........................ None
See application file for complete search history.

(56) References Cited

U.S. PATENT DOCUMENTS

| 6,140,049 | A | 10/2000 | Bachner et al. | |
|---|---|---|---|---|
| 2002/0198362 | A1* | 12/2002 | Gaiger et al. | ............... 530/350 |
| 2005/0059005 | A1 | 3/2005 | Tuschl et al. | |
| 2005/0074788 | A1 | 4/2005 | Dahlberg et al. | |
| 2005/0191632 | A1* | 9/2005 | Byrd et al. | ..................... 435/6 |
| 2009/0123533 | A1 | 5/2009 | Croce et al. | |

FOREIGN PATENT DOCUMENTS

| AU | 2003291433 B2 | 9/2008 |
|---|---|---|
| WO | WO 03/029459 A2 | 4/2003 |
| WO | WO 2004/057017 A2 | 7/2004 |
| WO | WO 2005/040419 A1 | 5/2005 |

OTHER PUBLICATIONS

Calin et al. A microRNA signature assoicated with prognosis and progression in chronic lymphocytic leukemia. N. Engl. J. Med. 353/793-801, 2005.*
Calin et al. MicroRNAs and leukemias: How strong is the connection. Leukemia Res. 30:653-655, 2006.*
Krosese et al. Genetic tests and their evaluation: Can we answer the key questions? Genet. Med. 6:475-480, 2004.*
Gura, T. Systems for identifying new drugs are oftern faulty. Science 278:1041-1042, 1997.*
Cimmino et al. miR-15 and miR-16 induce apoptosis by targeting BCL2. PNAS 102:13944-13949, 2005.*
Zeng, Y., et al., "Both Natural and Design Micro RNAs Can Inhibit the Expression of Cognate mRNAs When Expressed in Human Cells," *Mol. Cell*, 9:1327-1333 (2002).
Liu, Y., et al., "Cloning of Two Candidate Tumor Suppressor Genes Within a 10 kb Region on Chromosome 13q14, Frequently Deleted in Chronic Lymphocytic Leukemia," *Oncogene*, 15:2463-2473 (1997).

Bullrich, F., et al., "Characterization of the 13q14 Tumor Suppressor Locus in CLL: Identification of *ALT1*, an Alternative Splice Variant of the *LEU2* Gene," *Cancer Res.*, 61:6640-6648 (2001).
Migliazza, A., et al., "Nucleotide Sequence, Transcription Map, and Mutation Analysis of the 13q14 Chromosomal Region Deleted in B-Cell Chronic Lymphocytic Leukemia," *Blood*, 97(7):2098-2104 (2001).
Wolf, S., et al., "B-Cell Neoplasia Associated Gene with Multiple Splicing (*BCMS*): the Candidate B-CLL Gene on 13q14 Comprises More than 560 kb Covering All Critical Regions," *Hum. Mol. Genet.*, 10(12):1275-1285 (2001).
Mertens, D., et al., "Down-Regulation of Candidate Tumor Suppressor Genes within Chromosome Band 13q14.3 is Independent of the DNA Methylation Pattern in B-Cell Chronic Lymphocytic Leukemia," *Blood*, 99(11):4116-4121 (2002).
Bichi, R., et al., "Human Chronic Lymphocytic Leukemia Modeled in Mouse by Targeted *TCL1* Expression," *Proc. Natl. Acad. Sci. USA*, 99(10):6955-6960 (2002).
Lagos-Quintana, M., et al., "Identification of Novel Genes Coding for Small Expressed RNAs," *Science*, 294:853-858 (2001).
Lagos-Quintana, M., et al., "Identification of Tissue-Specific MicroRNAs From Mouse," *Curr. Biol.*, 12:735-739 (2002).
Lau, N. C., et al., "An Abundant Class of Tiny RNAs with Probable Regulatory Roles in *Caenorhabditis elegans*," *Science*, 294:858-862 (2001).
Ruvkun, G., "Glimpses of a Tiny RNA World," *Science*, 294:797-799 (2001).
Calin, G.A., et al., "Frequent Deletions and Down-Regulation of Micro-RNA Genes *miR15* and *miR16* at 13q14 in Chronic Lymphocytic Leukemia," *Proc. Natl. Acad. Sci. USA*, 99(24):15524-15529 (2002).
Xia, L., et al., "miR-15b and miR-16 Modulate Multidrug Resistance by Targeting BCL2 in Human Gastric Cancer Cells," *Int. J. Cance*, 123: 372-379 (2008).
Cho, W.C.S., "OncomiRs: The Discovery and Progress of MicroRNAs in Cancers," *Molecular Cancer*, 6:1-7 (2007).
Bonci, D., et al., "The *miR-15a-miR-16-1* Cluster Controls Prostate Cancer by Targeting Multiple Oncogenic Activities," *Nature Medicine* 14(11):1271-1277 (2008).
Calin, G.A. and Croce, C.M., "Genomics of Chronic Lymphocytic Leukemia MicroRNAs as New Players with Clinical Significance", *Seminars in Oncology*, 33:(2):167-173 (Apr. 1, 2006).
Verma, I.M., et al., "Gene Therapy: Twenty-First Century Medicine," *Annu. Revi. Biochem.* 74:711-738 (2005).
Romano, G., et al., "Latest Developments in Gene Transfer Technology," *Stem Cells* 18:19-39 (2000).
Dang, C.V., et al., "Gene Therapy and Translational Cancer Research," *Clin. Cancer Res.* 5:471-474 (1999).

* cited by examiner

*Primary Examiner*—Quang Nguyen
(74) *Attorney, Agent, or Firm*—Hamilton, Brook, Smith & Reynolds, P.C.

(57) ABSTRACT

The miR15 and miR16 micro RNA genes are located at 13q14 within a 30 kb region of loss characteristic of cells from certain cancers, such as cells from chronic lymphocytic leukemia or prostate cancer. Chronic lymphocytic leukemia or prostate cancer can be diagnosed by detecting a reduction in miR15 or miR16 gene copy number, by determining miR15 or miR16 gene mutational status, or by detecting a reduction in the RNA transcribed from these genes. The miR15 or miR16 gene products can inhibit the neoplastic or tumorigenic growth of cancers such as chronic lymphocytic leukemia or prostate cancer cells when administered to subjects suffering from these diseases.

10 Claims, 3 Drawing Sheets

```
          GAGUAAAGUA         UA           GA   U
5' CCUUG           GCAGCACA    AUGGUUUGUG   UUU  \
   GGAAC           CGUCGUGU   UACCGGACGU    AAA  G
       AUAAAAACUC          UA          GG      A
```

FIG. 1a

```
        AG   C            - A         CGUUA      UCUA
5' GUCAGC  UGC  UUAGCAGCAC  GU AAUAUUGG      AGAU       \
   CAGUUG  AUG  AGUCGUCGUG  CA UUAUGACC      UCUA       A
        GA   A           U    A       - - - - -     UUAA
```

FIG. 1b

SEQUENCE LISTING

<160> NUMBER OF SEQ ID NOS: 54

<210> SEQ ID NO 1
<211> LENGTH: 83
<212> TYPE: RNA
<213> ORGANISM: Homo sapiens

<400> SEQUENCE: 1
ccuuggagua aaguagcagc acauaauggu uuguggauuu ugaaaaggug caggccauau       60
ugugcugccu caaaaauaca agg                                              83

<210> SEQ ID NO 2
<211> LENGTH: 89
<212> TYPE: RNA
<213> ORGANISM: Homo sapiens

<400> SEQUENCE: 2
gucagcagug ccuuagcagc acguaaauau uggcguuaag auucuaaaau uaucuccagu       60
auuaacugug cugcugaagu aagguugac                                        89

<210> SEQ ID NO 3
<211> LENGTH: 22
<212> TYPE: RNA
<213> ORGANISM: Homo sapiens

<400> SEQUENCE: 3
uagcagcaca uaaugguuug ug                                               22

<210> SEQ ID NO 4
<211> LENGTH: 22
<212> TYPE: RNA
<213> ORGANISM: Homo sapiens

<400> SEQUENCE: 4
uagcagcacg uaaauauugg cg                                               22

<210> SEQ ID NO 5
<211> LENGTH: 23
<212> TYPE: DNA
<213> ORGANISM: Artificial Sequence
<220> FEATURE:
<223> OTHER INFORMATION: Probe

<400> SEQUENCE: 5
cacaaaccat tatgtgcttg cta                                              23

<210> SEQ ID NO 6
<211> LENGTH: 21

<212> TYPE: DNA
<213> ORGANISM: Artificial Sequence
<220> FEATURE:
<223> OTHER INFORMATION: Probe

<400> SEQUENCE: 6
gccaatattt acgtgctgct a                                          21

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
atacacctct aaatatctgt tccag                                      25

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
aagtaggacc attctaatag cc                                         22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gagtggcggt gagaaggtat                                            20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agccattgct atctttgagg                                            20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
tgggatatgc ttcagggac                                             19

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12

```
agctgacctt ggaatctggt t                                              21
```

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13

```
agatattgtc tccgttccat ga                                             22
```

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14

```
cccagatata aggacctggc ta                                             22
```

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15

```
cctggcctgt tagtttttat tgtta                                          25
```

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16

```
cccagtcttg ggtatgtttt ta                                             22
```

<210> SEQ ID NO 17
<211> LENGTH: 17
<212> TYPE: DNA
<213> ORGANISM: Artificial Sequence
<220> FEATURE:
<223> OTHER INFORMATION: Primer

<400> SEQUENCE: 17

```
gtttcgccaa gcctgtt                                                   17
```

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18

```
gttgacaata aaatacgcca ca                                             22
```

<210> SEQ ID NO 19
<211> LENGTH: 20
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<222> LOCATION: (1)...(20)
<223> OTHER INFORMATION: n = A,T,C or G

<400> SEQUENCE: 19
ctgnggcaaa aacaactctt                                              20

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
atctgtatgt cctcctttca atg                                          23

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
aacctcattt aaatgtaaag catca                                        25

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gtaatgtcat tgcttttgat ttgc                                         24

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ctcttgaggg aaaaaaaaaa tca                                          23

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ccaggcaacc aaccagtc                                                18

<210> SEQ ID NO 25
<211> LENGTH: 20
<212> TYPE: DNA
<213> ORGANISM: Artificial Sequence
<220> FEATURE:
<223> OTHER INFORMATION: Primer
```

<400> SEQUENCE: 25
atacagactt cccagtggct                                           20

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26
agctattaaa gttccctgga taaat                                     25

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
aaggaatcag agaaatgggg                                           20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gctgagtcag agggatttga                                           20

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
agaggtaaac aaaccaaacc c                                         21

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
gctgacaatc aagagaagat g                                         21

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
aaaatcaggt ggaaacagaa t                                         21

<210> SEQ ID NO 32
<211> LENGTH: 20

```
<212> TYPE: DNA
<213> ORGANISM: Artificial Sequence
<220> FEATURE:
<223> OTHER INFORMATION: Primer

<400> SEQUENCE: 32
aaaggctaac atcgaaggga                                             20

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
cagaaccaga gaaacagc                                               18

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
atggcacaac agcttaac                                               18

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
gaatgcaggt gtacctatca ac                                          22

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
actgagtgac tgctacccag                                             20

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
agctagccct atcagggt                                               18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
```

-continued gtaagtggag gttacctg                                            18

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
gaatcattcg tgctaagtgg at                                       22

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
tgccaactgc ttgaagaatc tc                                       22

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
acacctaact cctgggttgt tc                                       22

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
actaaatgcc agcgtttgca tg                                       22

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggtcttactc tggttaaatc t                                        21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
cattggtagc taaggaaaca c                                        21

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
ccattcaagc ctggacaatc tt					22

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
gaaacttgag acaataagga gc					22

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
catgtaacca agataaatcc gt					22

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
ctggaaaatg tatgtgatga gg					22

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
ctgttgctat ctgtaataac ac					22

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
cttggaattt tccactgaat c					21

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
tcatcagaag aaatcaaggc ag					22

-continued

```
<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
cagtgttagg aatacgcatt ca                                          22

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
ccttgccagt acgcccacaa gctg                                        24

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
ccccacctat ggttgtagtg agcatcc                                     27
```

COMPOSITIONS AND METHODS FOR CANCER DIAGNOSIS AND THERAPY

CROSS REFERENCE TO RELATED APPLICATIONS

This application is a continuation of U.S. application Ser. No. 10/706,798, filed Nov. 12, 2003, now abandoned, which claims the benefit of U.S. patent application 60/425,864, filed Nov. 13, 2002, and U.S. patent application 60/469,464, filed May 9, 2003. The entire teachings of the above applications are incorporated herein by reference.

REFERENCE TO GOVERNMENT GRANT

The invention described herein was supported in part by grant nos. P01CA76259, P01CA81534, and P30CA56036 from the National Cancer Institute. The U.S. government has certain rights in this invention.

FIELD OF THE INVENTION

The invention relates to the diagnosis of cancers, in particular to the diagnosis of chronic lymphocytic leukemias or prostate cancer by detecting miR15 and miR16 copy number, mutational status, or gene expression. The invention also relates to the treatment of cancers, involving the reduction or absence of miR15 or miR16 gene expression, in particular to the treatment of chronic lymphocytic leukemias or prostate cancer by administering miR15 or miR16 gene products.

BACKGROUND OF THE INVENTION

Cancers are a significant source of mortality and morbidity in the U.S. and throughout the world. In particular, chronic lymphocytic leukemia ("CLL") and prostate cancer are clinically important neoplastic diseases of adult humans. CLL is the most common form of adult leukemia in the Western world. Also, the age-adjusted incidence of prostate cancer now surpasses that of all other cancers among men in the United States, and, after lung cancer, is the second leading cause of all male cancer deaths in the country.

Hemizygous and/or homozygous loss at 13q14 occurs in more than half of the reported CLL cases, and constitutes the most frequent chromosomal abnormality in CLL. The karyotyping of tissue samples from CLL patients identified relatively few chromosomal abnormalities, suggesting that the specificity and frequency of observed deletions at 13q14 have pathologic significance. In addition, 13q14 deletions also occur in 60% of prostate cancers, suggesting that one or more tumor suppressor genes located at 13q14 are involved in the pathogenesis of both CLL and prostate cancers.

The presence of both clonal homozygous and heterozygous deletions, and the very high frequency of 13q14 loss in CLL and prostate cancers, indicates that deletions in this region are related to the etiology of certain cancer types. Several groups have used positional cloning in order to identify the gene or genes in the deleted areas. To date, a total of eight genes from the deleted regions of 13q14 in sporadic and familial cases of CLL have been identified and screened for alterations at the DNA and/or RNA level: Leu1 (BCMS or EST70/Leu1), Leu 2 (ALT1 or 1B4/Leu2), Leu 5 (CAR), CLLD6, KPNA3, CLLD7, LOC51131 (putative zinc finger protein NY-REN-34 antigen) and CLLD8. However, detailed genetic analyses, including extensive loss of heterozygosity (LOH), mutation and expression studies, have failed to demonstrate the consistent involvement of any of these genes in carcinogenesis.

Micro RNAs (miRNAs) are found in over one hundred distinct organisms, including fruit flies, nematodes and humans. miRNAs are believed to be involved in a variety of processes that modulate development in these organisms. The miRNAs are typically processed from 60- to 70-nucleotide foldback RNA precursor structures, which are transcribed from the miRNA gene. The RNA precursor or processed miRNA products are easily detected, and a lack of these molecules can indicate a deletion or loss of function of the corresponding miRNA gene.

Current therapies for CLL typically involve chemotherapy, administered alone or in combination with autologous bone marrow transplantation. The chemotherapy agents employed are generally toxic to the patient and cause only partial remissions in a relatively large proportion of patients. Therapies for prostate and other cancer therapies can also involve chemotherapy, often following surgical resection of a tumor. However, as with CLL, the curative properties of the chemotherapeutic agents (with or without surgery) are limited.

Prostate cancer can also be treated with external beam radiation or brachytherapy (e.g., with radioactive "seeds"), again either alone or in combination with surgery. Such treatments risk exposing normal tissue of the patient to the radiation, and may not be entirely effective.

There is a need for a rapid, economical and accurate diagnostic test for CLL or prostate cancer. There is also a need for an economical and effective treatment for cancers, especially CLL or prostate cancer, which does not have a significant negative impact on the patient.

SUMMARY OF THE INVENTION

It has now been discovered that the miR15 or miR16 genes are localized to 13q14 in humans, and that the 13q14 region is deleted in a significant portion of subjects suffering from CLL or prostate cancer. It has also been found that the RNA products of the miR15 or miR16 genes inhibit the neoplastic or tumorigenic growth of CLL and prostate cancer cells. The RNA products can be used as a therapy for cancers which involve downregulation of the miR15 or miR16 genes.

The miR15 and miR16 micro RNA genes are located at 13q14 within a 30 kb region of loss in CLL and prostate cancer, and both genes are deleted or down-regulated in the majority of CLL and prostate cancer cases. Thus, the invention provides a diagnostic test for CLL or prostate cancer comprising detection of the gene product from these genes, detection of miR15 or miR16 gene copy number, or determination of the mutational status.

In one embodiment, the diagnostic test comprises isolating RNA from a subject suspected of having CLL or prostate cancer, and detecting the levels of the miR15 or miR16 gene product by Northern blot hybridization using probes for miR15 or miR16 RNA precursor or processed miRNA, wherein a reduction in miR15 or miR16 precursor or processed microRNA as compared to a control normal sample is diagnostic of CLL or prostate cancer.

In another embodiment, the diagnostic test comprises isolating DNA from a subject suspected of having an miR15 or miR16 mediated cancer such as CLL or prostate cancer, and detecting the miR15 or miR16 gene copy number by Southern blot hybridization using probes for miR15 or miR16 gene sequences, wherein a reduction in gene copy number to one or zero is diagnostic of CLL or prostate cancer.

In another embodiment, the diagnostic test comprises detecting a reduction in miR15 or miR16 gene copy number by evaluating the loss of heterozygosity of the D13S273 and D13S272 markers, wherein a loss of heterozygosity at these markers is diagnostic of CLL or prostate cancer.

In a further embodiment, the diagnostic test comprises isolating DNA from a subject suspected of having CLL or prostate cancer, and detecting deletions or mutations in the miR15 or miR16 genes by PCR amplification of miR15 or miR16 gene fragments and comparing the amplified fragments with amplified fragments from a control normal sample, wherein the detection of a mutation in one or more copies of the miR15 or miR16 genes is diagnostic of CLL or prostate cancer. The amplified fragments can be compared by the single stranded conformational polymorphism technique. In one aspect the mutation is a partial deletion in the miR15 or miR16 gene sequences.

In another embodiment, the diagnostic test comprises isolating RNA from a subject suspected of having CLL or prostate cancer and detection of a mutation in miR15 or miR16 gene products is diagnostic of CLL or prostate cancer.

In a further embodiment, the diagnostic test comprises isolating RNA from a subject suspected of having CLL or prostate cancer, and detecting the levels of the miR15 or miR16 gene product by amplification of the miR15 or miR16 precursor or processed microRNA by reverse-transcriptase polymerase chain reaction, wherein a reduction in miR15 or miR16 precursor or processed microRNA as compared to an internal control amplified RNA is diagnostic of CLL or prostate cancer.

The invention also provides a method of treating an miR15 or miR16 mediated cancer in a subject in need of such treatment, comprising administering an effective amount of an miR15 or miR16 gene product to the subject, such that proliferation of cancer cells in inhibited.

The invention also provides a method of treating miR15 or miR16 mediated cancer in a subject in need of such treatment, in which cells from the subject are isolated and transfected ex vivo with an effective amount a nucleic acid comprising sequences encoding the miR15 or miR16 gene product. The expression of the miR15 or miR16 gene product in the transfected cells can be confirmed. The cells are then reimplanted into the subject, and proliferation of cancer cells in the subject is inhibited.

The invention further provides a method of inhibiting proliferation of miR15 or miR16 mediated cancer cells in a subject, comprising delivering to the cells an effective amount of an miR15 or miR16 gene product.

The invention still further provides a pharmaceutical composition for treating a subject having miR15 or miR16 mediated cancer, comprising an isolated miR15 or miR16 gene product, or a nucleic acid encoding an miR15 or miR16 gene product, and a pharmaceutically acceptable carrier.

BRIEF DESCRIPTION OF THE FIGURES

FIGS. 1A and 1B are schematic representations of the predicted secondary structure of the miR15 (SEQ ID NO:1) and miR16 (SEQ ID NO:2) precursor RNA, respectively. The RNA secondary structure prediction was performed using the "infold" program, version 3.1 of Matthews et al. (1999), *J. Mol. Biol.* 288:911-940, and manually refined to accommodate G/U wobble base pairs in the helical segments. The sequence of the processed miR15 (SEQ ID NO:3) and miR16 (SEQ ID NO:4) miRNA is underlined. Adapted from Lagos-Quintana et al. (2001), *Science* 294:853-858.

DETAILED DESCRIPTION OF THE INVENTION

Figures 2A, 2B, 2C, 2D:
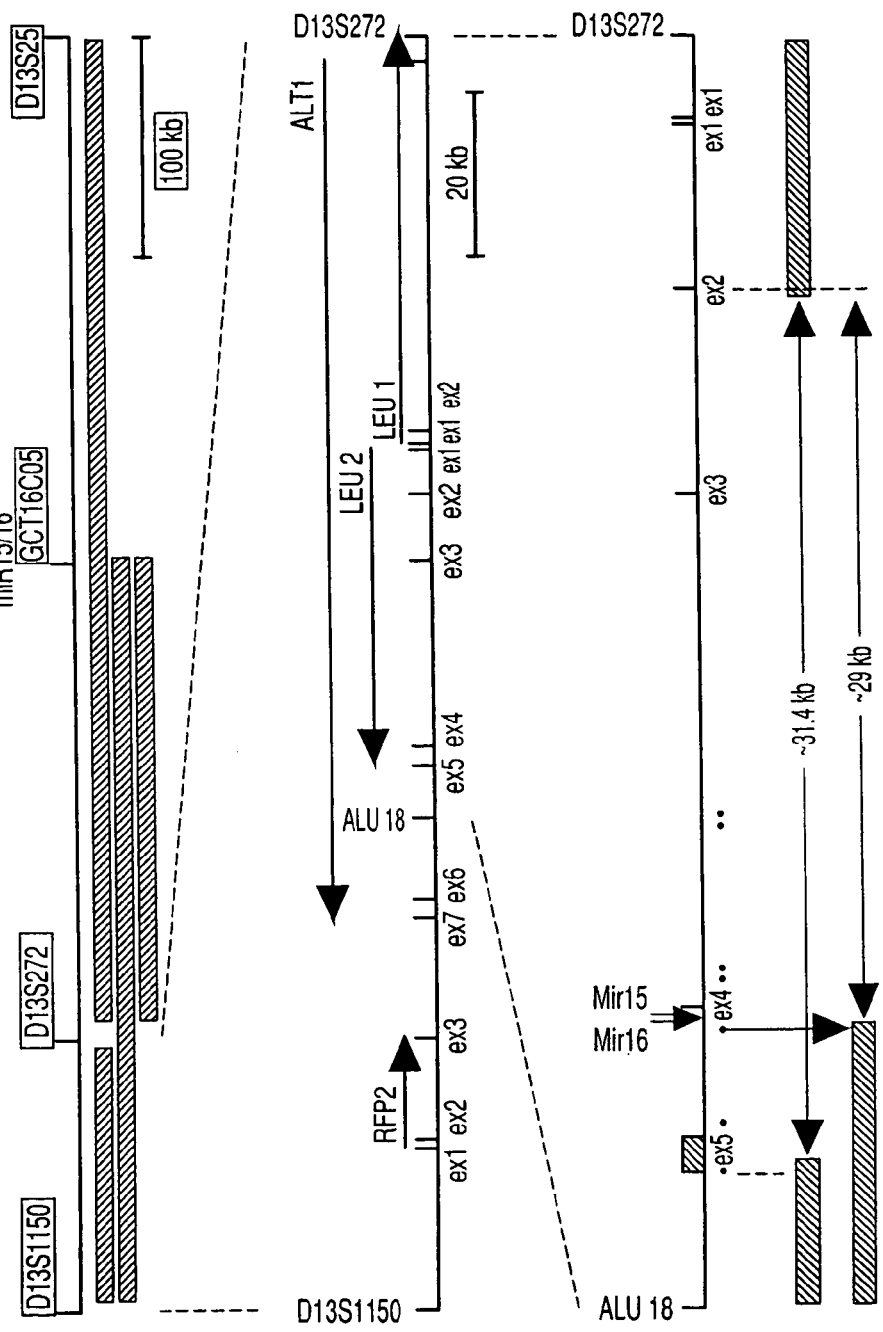
FIG. 2A is map of genes within the 13q14 tumor suppressor locus in CLL showing the localization of the miR15/16 gene cluster. The position of genetic markers and the position of genes on the map are shown.
FIG. 2B is a map of previously reported 13q14 deletions, marked by horizontally striped boxes.
FIG. 2C is a map of the locus between the D13S1150 and D13S272 markers. The orientation of each gene in this locus is marked by an arrow under the gene name, and colored vertical bars mark the position of corresponding exons for each gene.
FIG. 2D is a map of the locus between the Alu 18 and D13S272 markers. Bars and boxes mark the position of exons for LEU2/ALT1 and LEU1. The short vertical arrows mark the position of miR15 and miR16 genes. Circles mark the position of PCR primers used to screen somatic cell hybrid clones derived from a fusion of two independent leukemia cases (CLL-A and CLL-B). Filled boxes represent portions of chromosome 13 present in the hybrids. "←~31.4 kb→" indicates an approximately 31.4 kb deleted region in clone CLL-A, which was derived from a patient with CLL carrying a t(2;13)(q12;q13) translocation, bilateral retinoblastoma, and ulcerative colitis. The long vertical arrow represents the position of the breakpoint in clone CLL-B carrying a t(2;13)(q32;q14) translocation, and "←~29 kb→" indicates an approximately 29 kb deleted region in this clone.

All nucleic acid sequences herein are given in the 5' to 3' direction. In addition, all deoxyribonucleotides in a nucleic acid sequence are represented by capital letters (e.g., deoxythymidine is "T"), and ribonucleotides in a nucleic acid sequence are represented by lower case letters (e.g., uridine is "u").

CLL or prostate cancer can be diagnosed by detecting a reduction in miR15 or miR16 gene copy number, or by detecting mutations in one or more copies of the miR15 or miR16 genes. A reduction in miR15 or miR16 gene copy number from diploid to haploid, or to no copies, is diagnostic of CLL or prostate cancer. Likewise, a mutation in one or both copies of the miR15 or miR16 genes implies a loss of gene function, and is diagnostic of CLL or prostate cancer.

As used herein, a "CLL cell" is a lymphocyte from a subject who has or is suspected of having CLL, which lymphocyte has a "CLL Score" of at least 4 as determined according to the scoring system of Matutes et al. (1994), *Leukemia* 8(10):1640-1645, the entire disclosure of which is herein incorporated by reference. As used herein, a "prostate cancer cell" is a neoplastic or tumorigenic cell of prostate origin, whether or not located in the prostate. One skilled in the art can readily identify a CLL or prostate cancer cell.

The miR15/miR16 gene cluster has been mapped to 13q14. The nucleic acid sequences of these genes are contained within clone 317g11, the nucleotide sequence of which is given in GenBank record accession no. AC069475. The entire disclosure of that record is incorporated herein by reference. A deletion or mutation in the miR15 or miR16 genes can be detected by determining the structure or sequence of these genes in tissue from a subject suspected of having CLL or prostate cancer, and comparing this with the structure or sequence of these genes in a sample of unaffected tissue from the subject, or in a sample of tissue from a normal control. Such a comparison can be made by any suitable technique.

According to the practice of the invention, to diagnose an miR15 or miR16 mediated cancer, a tissue sample is derived from a subject. The sample is then prepared for determination of miR15 or miR16 gene product expression or deletion or mutation of miR15 or miR16 genes. A tissue sample includes a biopsy of interest, as well as blood and fluid samples.

As used herein, an "miR15 or miR16 mediated cancer" is any cancer in which the expression of the miR15 or miR16 genes is reduced or absent in at least a portion of tumorigenic or neoplastic cells associated with that cancer. Examples of miR15 or miR16 mediated cancers include CLL and prostate cancer.

The presence of miR15 or miR16 deletions or mutations can be detected by Southern blot hybridization of the genomic DNA from a subject, using probes for miR15 or miR16 genes, e.g., as described below. For example, a sample of tissue or blood can be removed from a subject suspected of having CLL or prostate cancer by conventional biopsy techniques. Alternatively, a blood sample can be removed from a subject suspected of having CLL or prostate cancer, and white blood cells isolated for DNA extraction. The blood or tissue sample is preferably obtained from the patient prior to initiation of radiotherapy or chemotherapy. A corresponding tissue or blood sample can be obtained from unaffected tissues of the subject, or from a normal human individual, for use as a control.

Southern blot hybridization techniques are within the skill in the art. For example, the genomic DNA isolated from tissue or blood from a subject suspected of having CLL or prostate cancer can be digested with restriction endonucleases. This digestion generates restriction fragments of the genomic DNA, which can be separated by electrophoresis, for example on an agarose gel. The restriction fragments are then blotted onto a hybridization membrane (e.g., nitrocellulose or nylon), and hybridized with labeled probes specific for the miR15 or miR16 genes. A deletion or mutation of these genes is indicated by an alteration of the restriction fragment patterns on the hybridization membrane, as compared to a control DNA sample which has been treated identically to the DNA sample from the subject. Probe labeling and hybridization conditions suitable for detecting miR15 or miR16 gene copy number or mutations can be readily determined by one of ordinary skill in the art. The term "deletion," as used herein, refers to partial deletion of a gene or to deletion of the entire gene.

The miR15 and miR16 nucleic acid probes for Southern blot hybridization can be designed based upon the published sequence of the miR15 and miR16 microRNAs as described in Lagos-Quintana et al. (2001), *Science* 294:853-858, the entire disclosure of which is incorporated herein by reference. The nucleotide sequence of the miR15 microRNA is uagcagcacauaauggguuugug (SEQ ID NO:3). The nucleotide sequence of the miR16 microRNA is uagcagcacguaaauauuggcg (SEQ ID NO:4). Suitable probes for detecting miR15 and miR16 DNA are, respectively:

```
CACAAACCATTATGTGCTTGCTA    (SEQ ID NO:5)

GCCAATATTTACGTGCTGCTA      (SEQ ID NO:6)
```

The complements of SEQ ID NO:5 and SEQ ID NO:6 can also be used to probe for miR15 or miR16 DNA.

Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11, the disclosures of which are herein incorporated by reference.

For example, the nucleic acid probe can be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are herein incorporated by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR15 or miR16 gene copy number. Alternatively, miR15 or miR16 gene copy number can be quantified by computerized imaging systems, such the Molecular Dynamics 400-B 2D Phosphorimager available from Amersham Biosciences, Piscataway, N.J.

Where radionuclide labeling of DNA or RNA probes is not practical, the random-primer method can be used to incorporate the dTTP analogue 5-(N—(N-biotinyl-epsilon-aminocaproyl)-3-aminoallyl)deoxyuridine triphosphate into the probe molecule. The biotinylated probe oligonucleotide can be detected by reaction with biotin-binding proteins such as avidin, streptavidin, or anti-biotin antibodies coupled with fluorescent dyes or enzymes which produce color reactions.

Deletions or mutations of the miR15 or miR16 genes can also be detected by amplifying a fragment of these genes by polymerase chain reaction (PCR), and analyzing the amplified fragment by sequencing or by electrophoresis to determine if the sequence and/or length of the amplified fragment from the subject's DNA sample is different from that of the control DNA sample. Suitable reaction and cycling conditions for PCR amplification of DNA fragments can be readily determined by one of ordinary skill in the art. Exemplary PCR reaction and cycling conditions are given in the methods used for the Examples, below.

Diagnosis of an miR15 or miR16 mediated cancer can be performed by detecting deletions of 13q14 between various chromosome markers, such as the markers indicated in FIGS. 1A, 1B, and 2A-2D. For example, a deletion in the region of 13q14 between microsatellite markers D13S272 and D13S273 comprising miR15 or miR16, indicates the presence of an miR15 or miR16 mediated cancer. In addition, when the deletion in 13q14 is between microsatellite markers D13S1150 and D13S273 or between locus Alu18 and microsatellite marker D13S273, where miR15 or miR16 are deleted, the presence of an miR15 or miR16 mediated cancer is indicated.

An alternative method of determining the number of miR15 or miR16 genes per diploid genome in a sample of tissue relies on the fact that the miR15/miR16 gene cluster is located in 13q14, and is linked to the markers D13S272 and D13S273. The loss of a copy of the miR15 or miR16 genes in an individual who is heterozygous at a locus linked to the D13S272 and D13S273 markers can be inferred from the loss of heterozygosity in these markers. Methods for determining loss of heterozygosity of chromosomal markers are within the skill in the art. An exemplary loss of heterozygosity study is given in Example 3 below.

Another technique for determining whether the miR15 or miR16 genes in a subject suspected of having CLL or prostate cancer are mutated is single strand conformational polymorphism (SSCP), for example as described in Orita et al. (1989), *Genomics* 5: 874-879 and Hayashi (1991), *PCR Methods and Applic.* 1: 34-38, the entire disclosures of which are herein incorporated by reference. The SSCP technique consists of amplifying a fragment of the gene of interest by PCR; denaturing the fragment and electrophoresing the two denatured single strands under non-denaturing conditions. The single strands assume a complex sequence-dependent intrastrand secondary structure that affects the strands electrophoretic mobility.

A deletion or mutation in one or both miR15 or miR16 genes can also cause a reduction in miR15 or miR16 gene expression. Thus, CLL or prostate cancer can also be diagnosed by detecting expression levels of the RNA produced from the miR15 or miR16 genes, where a reduction in miR15 or miR16 gene expression is diagnostic of CLL or prostate cancer.

The miR15 and miR16 genes are each transcribed to produce a ~70 kb precursor RNA which forms a stem-loop structure. The precursor RNA is not translated into a protein, but is rather processed into a "micro RNA" or "miRNA," which is believed to be the functional gene product.

As used herein, an "miR15 or miR16 gene product" means the processed or unprocessed RNA transcripts from the miR15 or miR16 genes, as described more fully below. The terms "RNA," RNA transcripts," and "gene product," are used interchangeably herein in the context of miR15 or miR16 gene expression.

The miR15 and miR16 precursor RNAs are described in Lagos-Quintana et al. (2001), *Science* 294, 853-858, the entire disclosure of which is incorporated herein by reference. The sequences of the miR15 and miR16 precursor RNAs are given in SEQ ID NO:1 and SEQ ID NO:2. The predicted stem-loop structures of SEQ ID NO:1 and SEQ ID NO:2, are shown in FIGS. 1A and 1B, respectively.

[SEQ ID NO:1]:
ccuuggaguaaaguagcagcacauaaugguuuguggauuuugaaaggug
caggccauauugugcugccucaaaaauacaagg

[SEQ ID NO:2]:
gucagcagugccuuagcagcacguaaauauuggcguuaagauucuaaaau
uaucuccaguauuaacugug cugcugaagu aagguugac Without wishing to be bound by any theory, it is believed that the miR15 and miR16 precursor RNAs are co-expressed from the miR15/miR16 gene cluster, and are processed by the Dicer/Argonaute complex into the functional miRNA products. See, e.g., Lee et al. (2001), *Science* 294:862. Both functional miRNA products from these genes are single-stranded RNA molecules of 22 nucleotides in length which have a 5' terminal monophosphate and a 3' terminal hydroxyl group. The nucleotide sequence of the processed miR15 microRNA is uagcagcacauaaugguuugug (SEQ ID NO:3). The nucleotide sequence of the processed miR16 microRNA is uagcagcacguaaauauuggcg (SEQ ID NO:4). In the practice of the invention, the 60-70 nt RNA precursor molecules produced from the miR15 or miR16 genes can be detected. Alternatively, the shorter miR15 and miR16 microRNA gene products, which are produced through processing of the precursor RNAs by the Dicer and Argonaute proteins, can be detected.

Methods for determining RNA expression levels are within the level of skill in the art. For example, a sample of tissue or blood from a subject suspected of having CLL or prostate cancer is obtained as described above. As a control, a corresponding tissue or blood sample can be obtained from unaffected tissues of the subject, or from a normal human individual as described above. The control tissue or blood sample is then processed along with the sample from the subject. The levels of miR15 or miR16 gene expression in the subject can then be compared to those from unaffected tissue from the subject, or to the miR15 or miR16 expression levels in tissue or blood from the normal control. For example, the relative miR15 or miR16 expression level in CLL cells or cells of the sampled prostate tumor are conveniently determined with respect to one or more standards. The standards may comprise, for example, a zero expression level on the one hand and the expression level of the gene in normal tissue of the same patient, or the expression level in the tissue of a normal control group on the other hand. The standard may also comprise the miR15 or miR16 expression level in a standard cell line. The size of the decrement in miR15 or miR16 expression in comparison to normal expression levels is indicative of the future clinical outcome following treatment.

Alternatively, the levels of miR15 or miR16 gene expression in a subject suspected of having CLL or prostate cancer can be compared to average levels of miR15 or miR16 gene expression previously obtained for a population of normal human controls.

Suitable techniques for determining the level of RNA transcripts of a particular gene in cells are well known to those skilled in the art. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7, the entire disclosure of which is incorporated by reference. Suitable probes for Northern blot hybridization of miR15 or miR16 RNA include SEQ ID NO:5 and SEQ ID NO:6.

Autoradiographic detection of probe hybridization to miR15 or miR16 RNA can be performed by exposing hybridized filters to photographic film. Densitometric scanning of the photographic films exposed by the hybridized filters provides an accurate measurement of RNA transcript levels. Alternatively, RNA transcript levels can be quantified by computerized imaging of the hybridization blot, for example with the Molecular Dynamics 400-B 2D Phosphorimager available from Amersham Biosciences, Piscataway, N.J.

In addition to Northern and other RNA blotting hybridization techniques, the levels of RNA transcripts can be carried out according to the technique of in situ hybridization. This technique requires fewer cells than the Northern blotting technique, and involves depositing whole cells onto a micro-scope cover slip and probing the nucleic acid content of the cell with a solution containing radioactive or otherwise labeled cDNA or cRNA probes. This technique is particularly well-suited for analyzing tissue biopsy samples from subjects suspected of having prostate cancer. The practice of the in situ hybridization technique is described in more detail in U.S. Pat. No. 5,427,916, the entire disclosure of which is incorporated herein by reference. Suitable probes for in situ hybridization of miR15 or miR16 RNA include SEQ ID NO:5 and SEQ ID NO:6.

The relative number of miR15 or miR16 transcripts can also be determined by reverse transcription of miR15 or miR16 transcripts, followed by amplification in a polymerase chain reaction (RT-PCR). The levels of miR15 or miR16 transcripts can be quantified in comparison with an internal standard, for example, levels of mRNA from a "housekeeping" gene present in the same sample. A suitable "housekeeping" gene for use as an internal standard includes myosin or glyceraldehyde-3-phosphate dehydrogenase (G3PDH). The methods for quantitative RT-PCR and variations thereof are well known to those of ordinary skill in the art.

Other techniques for measuring miR15 and miR16 expression are also known to those of skill in the art and include various techniques for measuring the rates of RNA transcription and degradation.

An miR15 or miR16 mediated cancer can be treated by administering the isolated gene product of the miR15 or miR16 genes, either alone or in combination, to an miR15 or miR16 mediated cancer cell. Without wishing to be bound by any theory, it is believed that the miR15 or miR16 gene products suppress the neoplastic or tumorigenic growth of such cancer cells.

In particular, CLL or prostate cancer can be treated by administering the isolated gene product of the miR15 or miR16 genes, either alone or in combination, to a CLL or prostate cancer cell.

As used herein, an "miR15 or miR16 mediated cancer cell" is a tumorigenic or neoplastic cell isolated from a subject suffering from an miR15 or miR16 mediated cancer. An miR15 or miR16 mediated cancer cell can be identified by detecting a reduction or absence of miR15 or miR16 gene products in the cell, or by detecting a cancerous or neoplastic phenotype in the cell. One skilled in the art can readily identify cells with a cancerous or neoplastic phenotype. For example, such cells are insensitive to contact-induced growth inhibition in culture, and will form foci when cultured for extended periods. Cancerous or neoplastic cells also exhibit characteristic morphological changes, disorganized patterns of colony growth and acquisition of anchorage-independent growth. Cancerous or neoplastic cells also have the ability to form invasive tumors in susceptible animals, which can be evaluated by injecting the cells, for example, into athymic mice using techniques within the skill in the art.

As used herein, an "isolated" gene product is one which is altered or removed from the natural state through human intervention. For example, an RNA naturally present in a living animal is not "isolated." A synthetic RNA, or an RNA partially or completely separated from the coexisting materials of its natural state, is "isolated." An isolated RNA can exist in substantially purified form, or can exist in a cell into which the RNA has been delivered. Thus, an miR15 or miR16 gene product which is deliberately delivered to or expressed in a cell, such as a CLL or prostate cancer cell, is considered an "isolated" gene product.

The miR15 and miR16 gene products can be obtained using a number of standard techniques. For example, the gene products can be chemically synthesized or recombinantly produced using methods known in the art. Preferably, the RNA products are chemically synthesized using appropriately protected ribonucleoside phosphoramidites and a conventional DNA/RNA synthesizer. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, the miR15 and miR16 gene products can be expressed from recombinant circular or linear DNA plasmids using any suitable promoter. Suitable promoters for expressing RNA from a plasmid include the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR15 and miR16 gene products in CLL, prostate cancer, or other cells.

The miR15 and miR16 gene products which are expressed from recombinant plasmids can be isolated from cultured cell expression systems by standard techniques. The miR15 and miR16 gene products which are expressed from recombinant plasmids can also be delivered to and expressed directly in the CLL or prostate cancer cells. The use of recombinant plasmids to deliver the miR15 and miR16 gene products to CLL or prostate cancer cells is discussed in more detail below.

The miR15 and miR16 gene products can be expressed from a separate recombinant plasmid, or can be expressed from the same recombinant plasmid. Preferably, the miR15 and miR16 gene products are expressed as the RNA precursor molecules from a single plasmid, and the precursor molecules are processed into the functional miRNA molecules by a suitable processing system. Suitable processing systems include the in vitro *Drosophila* cell lysate system as described in U.S. published application 2002/0086356 of Tuschl et al., the entire disclosure of which is herein incorporated by reference.

Selection of plasmids suitable for expressing the miR15 and miR16 gene products, methods for inserting nucleic acid sequences for expressing the gene products into the plasmid, and methods of delivering the recombinant plasmid to the cells of interest are within the skill in the art. See, for example Zeng et al. (2002), *Molecular Cell* 9:1327-1333; Tuschl (2002), *Nat. Biotechnol*, 20:446-448; Brummelkamp et al. (2002), *Science* 296:550-553; Miyagishi et al. (2002), *Nat. Biotechnol*. 20:497-500; Paddison et al. (2002), *Genes Dev.* 16:948-958; Lee et al. (2002), *Nat. Biotechnol*. 20:500-505; and Paul et al. (2002), *Nat. Biotechnol*. 20: 505-508, the entire disclosures of which are herein incorporated by reference.

In a preferred embodiment, a plasmid expressing the miR15 or miR16 gene products comprises a sequence encoding the miR15 or miR16 precursor RNA under the control of the CMV intermediate-early promoter. As used herein, "under the control" of a promoter means that the nucleic acid sequences encoding the miRNA product are located 3' of the promoter, so that the promoter can initiate transcription of the miRNA product coding sequences.

The miR15 or miR16 gene products can also be expressed from recombinant viral vectors. It is contemplated that the miR15 and miR16 gene products can be expressed from two separate recombinant viral vectors, or from the same viral vector. The RNA expressed from the recombinant viral vectors can either be isolated from cultured cell expression systems by standard techniques, or can be expressed directly in CLL or prostate cancer cells. The use of recombinant viral vectors to deliver the miR15 or miR16 gene products to CLL or prostate cancer cells is discussed in more detail below.

The recombinant viral vectors of the invention comprise sequences encoding the miR15 and miR16 gene products and any suitable promoter for expressing the RNA sequences. Suitable promoters include, for example, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR15 and miR16 gene products in a CLL or prostate cancer cell.

Any viral vector capable of accepting the coding sequences for the miR15 and miR16 gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like. Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therap.* 2:301-310; Eglitis (1988), *Biotechniques* 6:608-614; Miller (1990), *Hum. Gene Therap.* 1:5-14; and Anderson (1998), *Nature* 392:25-30, the entire disclosures of which are herein incorporated by reference.

Preferred viral vectors are those derived from AV and AAV. A suitable AV vector for expressing the miRNA of the invention, a method for constructing the recombinant AV vector, and a method for delivering the vector into target cells, are described in Xia et al. (2002), *Nat. Biotech.* 20:1006-1010, the entire disclosure of which is herein incorporated by reference. Suitable AAV vectors for expressing the miRNA of the invention, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. Preferably, the miR15 and miR16 gene products are expressed from a single recombinant AAV vector comprising the CMV intermediate early promoter.

In one embodiment, a recombinant AAV viral vector of the invention comprises a nucleic acid sequence encoding the miR15 or miR16 precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR15 or miR16 sequences from the vector, the polyT termination signals act to terminate transcription.

In the practice of the invention, the miR15 or miR16 gene products are used to inhibit the neoplastic or tumorigenic growth of miR15 or miR16 mediated cancer cells, in particular of CLL or prostate cancer cells. Without wishing to be bound by any theory, it is believed that the processed miR15 and miR16 miRNAs bind to complementary sequences in one or more target mRNAs which are necessary to initiate and/or maintain neoplastic or tumorigenic growth in these cells. Thus, the invention provides a method of treating an miR15 or miR16 mediated cancer, for example CLL or prostate cancer, in a subject in need of such treatment. The method comprises administering an effective amount of an miR15 or miR16 gene product to the subject, such that proliferation of miR15 or miR16 mediated cancer cells is inhibited.

As discussed above, an miR15 or miR16 mediated cancer is a cancer in which expression of either or both the miR15 or miR16 genes is reduced or absent in at least a portion of tumor or neoplastic cells associated with the disease. Expression of the miR15 or miR16 genes is reduced or absent in tumor or neoplastic cells from CLL or prostate cancer; thus, CLL and prostate cancer are considered to be miR15 or miR16 mediated cancers. A reduction or absence of miR15 or miR16 gene expression may also be found in other cancers; such cancers would therefore also be considered miR15 or miR16 mediated cancers.

For example, expression of the miR15 or miR16 genes may be reduced or absent in primary or metastatic tumor or neoplastic cells from cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia and chronic myelocytic leukemia).

Expression of the miR15 or miR16 genes may also be reduced or absent in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Expression of the miR15 or miR16 genes may also be reduced or absent in cancers or tumors in any prognostic stage of development, for example as measured by the "Overall Stage Groupings" (also called "Roman Numeral") or the "Tumor, Nodes, and Metastases" (TNM) staging systems. Appropriate prognostic staging systems and stage descriptions for a given cancer are known in the art, for example as described in the National Cancer Institute's "CancerNet" Internet website.

A subject in need of treatment for an miR15 or miR16 mediated cancer can be identified by obtaining a sample of tumor or neoplastic cells (or cells suspected of being tumor or neoplastic) from the subject, and determining whether the expression of miR15 or miR16 is reduced or absent in at least a portion of the cells as compared to cells from normal tissue obtained from the subject. Methods for detecting miR15 or miR16 gene expression levels in cells are within the skill in the art (see above). Alternatively, the miR15 or miR16 expression in cells obtained from a subject can be compared to average expression levels of these genes in cells obtained from a population of normal subjects. A subject in need of treatment for CLL can be readily identified by a physician using standard diagnostic techniques. See, e.g., "Chronic lymphocytic leukemia: recommendations for diagnosis, staging, and response criteria. International Workshop on Chronic Lymphocytic Leukemia," (1989) *Annals of Internal Medicine* 110(3):236-238, the entire disclosure of which is herein incorporated by reference. For example, subjects with CLL exhibit circulating CLL cells, lymphocytosis (i.e., lymphocyte counts in the blood equal to or higher than 10,000 cells per cubic millimeter), and a progressive accumulation of CLL cells in the bone marrow and lymphatic tissues.

The identity of CLL cells in a subject's blood or other tissue can be confirmed by direct visual observation of a blood sample, and/or by determining the "CLL Score" of lymphocytes. The CLL Score indicates the presence or absence of five lymphocyte surface markers characteristic of CLL cells: CD5+, CD23+, FMC7−, and weak expression (+/−) of surface immunoglobulin (SmIg) and CD22. This scoring system gives a value of 1 or 0 for each of these five markers according to whether it is typical or atypical for CLL. CLL cells have a CLL Score 4 or 5, while lymphocytes from other leukemias have a CLL Score of <1 to 3. See Matutes et al. (1994), *Leukemia* 8(10):1640-1645 and Moreau et al. (1997), *American Journal of Clinical Pathology,* 108:378-82, the entire disclosures of which are herein incorporated by reference. CLL cells also have relatively low levels of surface-membrane immunoglobulin as compared with normal peripheral blood B cells. Surface-membrane immunoglobulin levels on lymphocytes can be readily detected according to standard techniques; see, e.g., Rozman et al. (1995), *New England Journal of Medicine* 333:1052-1057, the entire disclosure of which is herein incorporated by reference.

A subject in need of treatment for prostate cancer can also be readily identified by a physician according to standard diagnostic techniques, using criteria such as patient age, detection of an enlarged prostate by digital rectal exam, prostate-specific antigen ("PSA") level, Gleason score of biopsy material, and the presence of immunohistochemically detectable genetic markers such as p53, p21, and cyclins on cells from prostate tissue. A serum PSA level of 20 ng/ml or greater and a poorly differentiated prostate tissue histology (e.g., Gleason score 8 or higher) is indicative of prostate cancer. The presence of prostate tumors in a subject can also be confirmed by non-invasive imaging techniques, such as CT scan, transrectal ultrasound of the prostate ("TRUSP"), and magnetic resonance imaging ("MRI"), as are known in the art.

As used herein, an "effective amount" of miR15 or miR16 gene products is an amount sufficient to inhibit proliferation of an miR15 or miR16 mediated cancer cell in a subject suffering from an miR15 or miR16 mediated cancer. For example, an effective amount of miR15 or miR16 gene products can be an amount sufficient to inhibit proliferation of CLL cells in a subject suffering from CLL, or inhibit proliferation of prostate cancer cells in a subject suffering from prostate cancer. It is understood that a "prostate tumor cell" is not necessarily located in the prostate, but includes cells from metastatic tumors of prostate origin.

As used herein, to "inhibit the proliferation of an miR15 or miR16 mediated cancer cell" means to kill the cell, or permanently or temporarily arrest the growth of the cell. Inhibition of miR15 or miR16 mediated cancer cell proliferation can be inferred if the number of such cells in the subject remains constant or decreases after administration of the miR15 or miR16 gene products. An inhibition of miR15 or miR16 mediated cancer cell proliferation can also be inferred if the absolute number of such cells increases, but the rate of tumor growth decreases.

The number of miR15 or miR16 mediated cancer cells in a subject's body can be determined by direct measurement, or by estimation from the size of primary or metastatic tumor masses.

For example, the number of CLL cells in a subject can be readily determined, for example by a whole blood or white blood cell count. The number of CLL cells can also be readily determined by immunohistological methods, flow cytometry, or other techniques designed to detect the characteristic surface markers of CLL cells.

The size of a prostate tumor mass or a tumor mass can be ascertained by direct visual observation, or by diagnostic imaging methods such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument such as a caliper. For prostate tumors, a preferred physical means for determining the size of a tumor mass is the digital rectal exam.

One skilled in the art can readily determine an effective amount of the miR15 or miR16 gene products to be administered to a given subject, by taking into account factors such as the size and weight of the subject; the extent of disease penetration; the age, health and sex of the subject; the route of administration; and whether the administration is regional or systemic.

For example, an effective amount of the compounds of the invention can be based on the approximate weight of a tumor mass to be treated. The approximate weight of a tumor mass can be determined by calculating the approximate volume of the mass, wherein one cubic centimeter of volume is roughly equivalent to one gram. An effective amount of the miR15 or miR16 gene products based on the weight of a tumor mass can be at least about 10 micrograms/gram of tumor mass, and is preferably between about 10-500 micrograms/gram of tumor mass. More preferably, the effective amount is at least about 60 micrograms/gram of tumor mass. Particularly preferably, the effective amount is at least about 100 micrograms/gram of tumor mass. It is preferred that an effective amount based on the weight of the tumor mass be injected directly into the tumor.

An effective amount of the miR15 or miR16 gene products can also be based on the approximate or estimated body weight of a subject to be treated. Preferably, such effective amounts are administered parenterally or enterally, as described below. For example, an effective amount of the miR15 or miR16 gene products administered to a subject can range from about 5-3000 micrograms/kg of body weight, and is preferably between about 700-1000 micrograms/kg of body weight, and is more preferably greater than about 1000 micrograms/kg of body weight.

One skilled in the art can also readily determine an appropriate dosage regimen for the administration of the miR15 and miR16 gene products to a given subject. For example, the miR15 and miR16 gene products can be administered to the subject once (e.g., as a single injection or deposition). Alternatively, the gene products can be administered once or twice daily to a subject for a period of from about three to about twenty-eight days, more preferably from about seven to about ten days. In a preferred dosage regimen, the miR15 and miR16 gene products are administered once a day for seven days. Where a dosage regimen comprises multiple administrations, it is understood that the effective amount of the miR15 and miR16 gene products administered to the subject can comprise the total amount of gene product administered over the entire dosage regimen.

The miR15 and miR16 gene products can be administered to a subject by any means suitable for delivering the gene products to cells of the subject, such as hematopoietic stem cells (HSCs), CLL cells or prostate cancer cells. For example, the miR15 and miR16 gene products can be administered by methods suitable to transfect cells of the subject with miR15 or miR16 gene products, or with nucleic acids comprising sequences encoding the miR15 or miR16 gene products. The cells can be transfected directly with the miR15 or miR16. gene products (as these are nucleic acids), or can be transfected with nucleic acids comprising sequences encoding the miR15 or miR16 gene products. Preferably, the cells are transfected with a plasmid or viral vector comprising sequences encoding the miR15 or miR16 gene products, as described above.

Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer—Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

In one embodiment, miR15 or miR16 mediated cancer cells, for example CLL or prostate cancer cells, are isolated from the subject, transfected with nucleic acids encoding the miR15 and miR16 gene products, and reintroduced into the subject. In a preferred embodiment, the transfected and reimplanted cells are CLL cells. In a particularly preferred embodiment, the transfected and reimplanted cells are HSCs from a subject who has been diagnosed with CLL.

Techniques for isolating CLL cells from a subject are within the skill in the art, for example as described in Example 7 below. Techniques for isolating, identifying, separating, and culturing HSCs from a subject are also within the skill in the art, for example as disclosed in U.S. Pat. Nos. 5,635,387 and 5,643,741, and Campana et al. (1995) *Blood* 85:1416-1434, the entire disclosures of which are incorporated herein by reference. Preferably, harvested bone marrow is purged of tumorigenic or neoplastic cells prior to transfection of the HSCs. Suitable purging techniques include, for example, leukopheresis of mobilized peripheral blood cells, immunoaffinity-based selection or killing of tumor cells, or the use of cytotoxic or photosensitizing agents to selectively kill tumor cells, as are known in the art. See, for example, *Bone Marrow Processing and Purging*, Part 5 (A. Gee, ed.), CRC Press, Boca Raton, Fla., 1991; Lydaki et al. (1996) *J. Photochem. and Photobiol.* 32:27-32; and Gazitt et al. (1995), *Blood,* 86:381-389, the entire disclosures of which are herein incorporated by reference.

The isolated CLL cells or HSCs can be transfected by any suitable technique, as discussed above. After transfection, a portion of the CLL cells or HSCs can be examined to confirm the presence of appropriate expression levels of the gene products. Once appropriate expression of miR15 or miR16 gene products has been confirmed, the remaining transfected cells can then be reintroduced into the subject. Transfected CLL cells or HSCs can be reintroduced into the subject by parenteral methods, including intravenous infusion or direct injection into the bone marrow. The transfected cells are preferably reintroduced into the subject in a saline solution or other pharmaceutically acceptable carrier. A suitable number of transfected cells for reintroduction is from about $10^5$ to about $10^8$ cells per kilogram of subject body weight. The number of transfected cells available for re-introduction can be increased by expanding the cells in culture prior to transfection.

Preferably, the CLL cells or HSCs are transfected with a nucleic acid comprising sequences which encode an miR15 or miR16 gene product, e.g. a plasmid expression vector, that stably integrates into the CLL cell or HSC genome to provide long-term expression of the compound. Stable integration and expression can be confirmed by techniques known in the art, such as a Southern blot of genomic DNA using miR15 or miR16 cDNA (or fragments thereof) as a probe. Expression of miR15 or miR16 gene products can also be detected by standard Northern blot techniques. The CLL cells or HSCs stably transfected with sequences encoding the miR15 or miR16 gene products continue to express the compound once they are re-implanted into the subject. An exemplary method of isolating HSC from a subject, transfecting them with plasmids expressing miR15 and miR16 gene products, and reimplanting the transfected HSC into the subject is given in Example 8 below.

The miR15 and miR16 gene products can also be administered to a subject by any suitable enteral or parenteral administration route. Suitable enteral administration routes for the present methods include oral, rectal, or intranasal delivery. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection (e.g., peri-tumoral and intratumoral injection, intra-retinal injection, or subretinal injection); subcutaneous injection or deposition including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Preferably, the miR15 and miR16 gene products are administered by injection or infusion. For the treatment of miR15 or miR16 mediated cancers which involve solid tumors, the miR15 and miR16 gene products are preferably administered by direct injection into the tumor.

In the present methods, the miR15 and miR16 gene products can be administered to the subject either as naked RNA, in conjunction with a delivery reagent, or as a nucleic acid (e.g., a recombinant plasmid or viral vector) comprising sequences which expresses the gene product. Suitable delivery reagents for administration of the miR15 and miR16 gene products include the Mirus Transit TKO lipophilic reagent; lipofectin; lipofectamine; cellfectin; or polycations (e.g., polylysine), or liposomes.

Recombinant plasmids comprising sequences which express the miR15 or miR16 gene products are discussed above. Recombinant viral vectors comprising sequences which expresses the miR15 or miR16 gene products are also discussed above, and methods for delivering such vectors to CLL or prostate cancer cells of a subject are within the skill in the art.

In a preferred embodiment, liposomes are used to deliver the miR15 or miR16 gene products, or nucleic acids comprising sequences encoding the gene products, to a subject. Liposomes can also increase the blood half-life of the gene products or nucleic acids. In the practice of this embodiment of the invention, the miR15 or miR16 gene products, or nucleic acids comprising sequences encoding the gene products, are encapsulated in liposomes prior to administration to the subject.

Liposomes suitable for use in the invention can be formed from standard vesicle-forming lipids, which generally include neutral or negatively charged phospholipids and a sterol such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes encapsulating the miR15 or miR16 gene products, or nucleic acids comprising sequences encoding the gene products, can comprise a ligand molecule that targets the liposome to an miR15 or miR16 mediated cancer cell, such as a CLL or prostate cancer cell. Ligands which bind to receptors prevalent in such cancer cells, such as monoclonal antibodies that bind to tumor cell antigens or CLL cell surface markers, are preferred.

The liposomes encapsulating the miR15 or miR16 gene products, or nucleic acids comprising sequences encoding the gene products, can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), *Proc. Natl. Acad. Sci., USA,* 18: 6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR15 or miR16 gene products, or nucleic acids comprising sequences encoding the gene products, to tumor cells.

The miR15 or miR16 gene products are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science,* 17th ed., Mack Publishing Company, Easton, Pa. (1985), the entire disclosure of which is herein incorporated by reference.

The present pharmaceutical formulations comprise the miR15 or miR16 gene products, or a nucleic acid comprising sequences encoding the gene products (e.g., 0.1 to 90% by weight), or a physiologically acceptable salt thereof, mixed with a pharmaceutically-acceptable carrier. The pharmaceutical formulations of the invention can also comprise the miR15 or miR16 gene products, or nucleic acids comprising gene products encoding the gene products, which are encapsulated by liposomes and a pharmaceutically-acceptable carrier.

Preferred pharmaceutically-acceptable carriers are water, buffered water, normal saline, 0.4% saline, 0.3% glycine, hyaluronic acid and the like.

In a preferred embodiment, the pharmaceutical compositions of the invention comprise miR15 or miR16 gene products which are resistant to degradation by nucleases. One skilled in the art can readily synthesize miR15 and miR16 gene products which are nuclease resistant, for example by incorporating one or more ribonucleotides which are modified at the 2' position into the miR15 and miR16 gene products. Suitable 2'-modified ribonucleotides include those modified at the 2'-position with fluoro, amino, alkyl, alkoxy, and O-allyl.

For example, the pharmaceutical compositions of the invention comprise miR15 or miR16 gene products incorporating one or more 2'-modified ribonucleotides of the formulae 2'AR-nucleotide, wherein:

A is oxygen or a halogen (preferably fluorine, chlorine or bromine); and

R is hydrogen or straight or branched chain $C_{1-6}$ alkyl;

provided that when A is a halogen, then X and R are omitted. A preferred modified 2-ribonucleotide is 2'-O methyl ribonucleotide. Preferably, pharmaceutical compositions of the invention comprise miR15 or miR16 gene products in which each ribonucleotide is a 2'-modified ribonucleotide.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the miR15 or miR16 gene products. A pharmaceutical composition for aerosol (inhalational) administration can comprise 0.01-20% by weight, preferably 1%-10% by weight, of the miR15 or miR16 gene products encapsulated in a liposome as described above, and a propellant. A carrier can also be included as desired; e.g., lecithin for intranasal delivery.

The invention will now be illustrated by the following non-limiting examples.

EXAMPLES

The following techniques were used in the Examples:

Patient samples and cell lines—Patient samples were obtained after informed consent from patients diagnosed with CLL at the CLL Research Consortium institutions. Briefly, peripheral blood was obtained from CLL patients, and mononuclear cells were isolated through Ficoll-Hypaque gradient centrifugation (Amersham Pharmacia Biotech, Piscataway, N.J.) and then processed for RNA and DNA extraction according to standard protocols as described in Sambrook J et al. (1989), *Molecular cloning: A Laboratory Manual* (Cold Spring Harbor Laboratory Press, Cold Spring Harbor, N.Y.), the entire disclosure of which is herein incorporated by reference. As normal controls for LOH studies, DNA from buccal mucosa from the corresponding patients was included on small (1-2 mm²) pieces of paper.

Thirty human cell lines were obtained from the American Type Culture Collection (ATCC; Manassas, Va.) and maintained according to ATCC instructions. These cell lines were AS283, BL2, Bla, BJAB, CA46, Namalva, P3HRI, PAPB 682, PABm, Raji (Burkitt's lymphoma), Dell, SKDHL, ST486 (T-cell lymphoma), JM (immunoblastic B cell lymphoma), MC116 (undifferentiated lymphoma), Molt3, Supt 11 (T-ALL), U266 (multiple myeloma), A549, H1299 (lung carcinoma), TE2, TE10 (esophageal carcinoma), HeLa (cervical carcinoma), RC48 (kidney carcinoma) and 2220, 2221, 11609, 11611, LNCAP, TSUR (prostate carcinoma).

CD5+ B-cell separation—Tonsils were obtained from patients in the pediatric age group (3-9 years) undergoing routine tonsillectomies. Purified B cells were obtained by rosetting the mononuclear cells with neuraminidase treated sheep erythrocytes. The B cells were further fractionated by discontinuous Percoll gradients (Pharmacia Biotech, Uppsala, Sweden) as described in Dono M et al. (2000), *J. Immunol.* 164:5596-5604, the entire disclosure of which is herein incorporated by reference. The B cells collected from the 50% Percoll fraction were incubated with anti CD5 mAb followed by goat anti mouse Ig conjugated with magnetic microbeads. CD5+ B cells were obtained by positive selection by collecting the cells retained on the magnetic column MS using the MiniMACS system (Miltenyi Biotec).

Somatic cell hybrids—Somatic cell hybrids were generated following conventional methods and selected in hypoxanthine-aminopterin-thymidine (HAT) medium as described in Negrini M et al. (1994), *Cancer Res.* 54:1818-1824, the entire disclosure of which is herein incorporated by reference. DNA derived from single cell clones and subclones was isolated with the DNeasy tissue kit (Qiagen) and screened by PCR for the presence or absence of chromosome 13 and chromosome 2 markers (see Table 1 below for primer sequences). Fifteen clones were isolated from fusion of a CLL case (CLL-B) carrying a t(2;13)(q32; q14) translocation, and one clone was isolated from fusion of another CLL case (CLL-A) carrying a t(2;13)(q12; q13) translocation. Twelve CLL-B derived clones carried a full complement of both chromosomes 13 and 2, whereas three carried the del (13q) and a full complement of chromosome 2. The single clone from CLL-A carried a chromosome 13 with a small deletion at 13q14 and no part of chromosome 2.

Northern blotting—Total RNA isolation was performed using the Tri-Reagent protocol (Molecular Research Center, Inc). RNA samples (30 µg each) were run on 15% acrylamide denaturing (urea) Criterion precast gels (Bio-Rad Laboratories, Hercules, Calif.) and then transferred onto Hybond-N+ membrane (Amersham Pharmacia Biotech). The hybridization with $\alpha$-$^{32}$P ATP was performed at 42° C. in 7% SDS, 0.2M Na2PO4 pH 7.0 overnight. Membranes were washed at 42° C., twice in 2× SSPE, 0.1% SDS and twice with 0.5× SSPE, 0.1% SDS. The probes used to detect miR15 and miR16 RNA were, respectively:

```
CACAAACCATTATGTGCTTGCTA      (SEQ ID NO:5)

GCCAATATTTACGTGCTGCTA        (SEQ ID NO:6)
```

Blots were stripped by boiling in 0.1% aqueous SDS/0.1× SSC for 10 minutes, and were reprobed several times. As loading control, 5S rRNA stained with ethidium bromide was used.

Reverse Transcriptase Polymerase Chain Reaction (RT-PCR)—RT-PCR was performed to analyze the levels of gene expression in normal CD5+ cells and 23 B-CLL samples. One microliter of cDNA was used for each amplification reaction using,the Advantage2 PCR kit (Clontech), with 10 pmol of each gene-specific primer for 35 cycles of 94° C. for 20 seconds, 65° C. for 30 seconds, 68° C. for 1 minute (for a list of primers used, see Table 1 below). To ensure that the RNA was of sufficient purity for RT-PCR, a PCR assay with primers specific for G3PDH cDNA (Clontech, Palo Alto, Calif.)

was used. RT-PCR products were separated by agarose gel electrophoresis following standard procedures as described in Sambrook J et al. (1989), supra.

Western blotting—SDS/PAGE gels of cell lysates from 9 B-CLL patients were probed with GST-SLUG Middle antibody (a gift from Dr. Thomas Look—Harvard, Mass.) and SNX2 (N17) antibody (Santa Cruz Biotechnology, Calif.). Detection was performed using ECL Western Blotting detection kit (Amersham Pharmacia, UK) according to the manufacturer's instructions.

Database analysis—Searches against the "nr" and "dbEST" databases, and a search for short, nearly exact matches were performed with the BLAST alignment tool accessed through the National Center for Biotechnology Information website, maintained by the National Institutes of Health and the National Library of Medicine. See also Altschul et al. (1990), *J. Mol. Biol.* 215: 403-10 and Altschul et al. (1997), *Nucleic Acids Res.* 25:3389-3402, the entire disclosures of which are herein incorporated by reference. Searches for homology of short sequences were also performed with the FASTA alignment tool provided by the Biology work-Bench website.

TABLE 1

Primers Used for Screening Somatic Cell Hybrids

| Name | Primer Sequence | SEQ ID NO. |
|---|---|---|
| D2S396L | ATA CAC CTC TAA ATA TCT GTT CCA G | 7 |
| D2S396R | AAG TAG GAC CAT TCT AAT AGC C | 8 |
| D2S112L | GAG TGG CGG TGA GAA GGT AT | 9 |
| D2S112R | AGC CAT TGC TAT CTT TGA GG | 10 |
| D2S2243L | TGG GAT ATG CTT CAG GGA C | 11 |
| D2S2243R | AGC TGA CCT TGG AAT CTG GTT | 12 |
| D13S260L | AGA TAT TGT CTC CGT TCC ATG A | 13 |
| D13S260R | CCC AGA TAT AAG1 GAC CTG GCT A | 14 |
| D13S263L | CCT GGC CTG TTA GTT TTT ATT GTT A | 15 |
| D13S263R | CCC AGT CTT GGG TAT GTT TTT A | 16 |
| D13S165L | GTT TCG CCA AGC CTG TT | 17 |
| D13S165R | GTT GAC AAT AAA ATA CGC CAC A | 18 |
| D13S273L | CTG NGG CAA AAA CAA CTC TT | 19 |
| D13S273R | ATC TGT ATG TCC TCC TTT CAA TG | 20 |
| D13S1168L | AAC CTC ATT TAA ATG TAA AGC ATC A | 21 |
| D13S1168R | GTA ATG TCA TTG CTT TTG ATT TGC | 22 |
| DI3S1150L | CTC TTG AGG GAA AAA AAA AAT CA | 23 |
| DI3S1150R | CCA GGC AAC CAA CCA GTC | 24 |
| D13S272L | ATA CAG ACT TCC CAG TGG CT | 25 |
| D13S272R | AGC TAT TAA AGT TCC CTG GAT AAA T | 26 |
| GCT16C05L | AAG GAA TCA GAG AAA TGG GG | 27 |
| GCT16C05R | GCT GAG TCA GAG GGA TTT GA | 28 |
| D13S25FOR | AGA GGT AAA CAA ACC AAA CCC | 29 |

TABLE 1-continued

Primers Used for Screening Somatic Cell Hybrids

| Name | Primer Sequence | SEQ ID NO. |
|---|---|---|
| D13S25REV | GCT GAC AAT CAA GAG AAG ATG | 30 |
| D13S284L | AAA ATC AGG TGG AAA CAG AAT | 31 |
| D13S284R | AAA GGC TAA CAT CGA AGG GA | 32 |
| 01ALU18 | CAG AAC CAG AGA AAC AGC | 33 |
| 02ALU18 | ATG GCA CAA CAG CTT AAC | 34 |
| AFMA301WB5 | GAA TGC AGG TGT ACC TAT CAA C | 35 |
| AFMA301WB5 | ACT GAG TGA CTG CTA CCC AG | 36 |
| D13S272L1 | AGC TAG CCC TAT CAG GGT | 37 |
| D13S272R1 | GTA AGT GGA GGT TAC CTG | 38 |
| 5279F | GAA TCA TTC GTG CTA AGT GGA T | 39 |
| 5451R | TGC CAA CTG CTT GAA GAA TCT C | 40 |
| 7130F | ACA CCT AAC TCC TGG GTT GTT C | 41 |
| 7371R | ACT AAA TGC CAG CGT TTG CAT G | 42 |
| 9530F | GGT CTT ACT CTG GTT AAA TCT | 43 |
| 9757R | CAT TGG TAG CTA AGG AAA CAC | 44 |
| 11521F | CCA TTC AAG CCT GGA CAA TCT T | 45 |
| 11802R | GAA ACT TGA GAC AAT AAG GAG C | 46 |
| 12440F | CAT GTA ACC AAG ATA AAT CCG T | 47 |
| 12558R | CTG GAA AAT GTA TGT GAT GAG G | 48 |
| 17261F | CTG TTG CTA TCT GTA ATA ACA C | 49 |
| 17494R | CTT GGA ATT TTC CAC TGA ATC | 50 |
| 18701R | TCA TCA GAA GAA ATC AAG GCA G | 51 |
| 18560F | CAG TGT TAG GAA TAC GCA TTC A | 52 |
| GSP2F4 | CCT TGC CAG TAC GCC CAC AAG CTG | 53 |
| GSP1R1 | CCC CAC CTA TGG TTG TAG TGA GCA TCC | 54 |

Example 1

A 30 kb Deletion Region in Somatic Cell Hybrids of CLL Patients

Heretofore, there has been no clear definition of the minimal region of loss at 13q14 in CLL patients. Previously, various and relatively large (between 130 to 550 kb) regions deleted in 13q14 have been described in CLL (see FIG. 2B). LOH and Southern blot analyses were used to identify the centromeric boundary of homozygous loss at the Alu18 locus (FIG. 2D), which is located between D13S1150 and D13S272 less than 65 kb centromeric to exon 5 of the LEU2 gene. However, no small or overlapping homozygous deletions were found that allowed a better localization of the target tumor suppressor.

To better define the region of loss in CLL, somatic cell hybrids of mouse LM-TK⁻ and CLL cells carrying 13q14 translocations and/or deletions were generated. PCR screening of resulting hybrid clones allowed the segregation of the two copies of chromosome 13 present in the tumors. In this manner, a 31.4 kb deletion was identified in one case, and the chromosomal breakpoint was precisely localized in the other (FIG. 2D). These results indicated that the 13q14 tumor suppressor genes lay within a 29 kb region between exons 2 and 5 of the LEU2 gene. The primers used to screen the somatic cell hybrids are given in Table 1.

As shown in FIG. 2, the region deleted in the somatic cell hybrids was consistent with all reported regions of loss, including a 10 kb region reported several years ago by Liu et al. (1997) *Oncogene* 15:2463-2473. Exons 1 and 2 of LEU2 also lay within that region, and within the one defined here. However, LEU2 has been excluded as a likely candidate tumor suppressor gene for B-CLL (see Bullrich et al. (2001), *Cancer Res.* 61:6640-6648; Migliazza et al. (2001), *Blood* 97:2098-2104; Wolf et al. (2001), *Hum. Mol. Genet.* 10:1275-1285; and Mertens et al. (2002) *Blood* 99:4116-4121).

Example 2

Figure 3A:
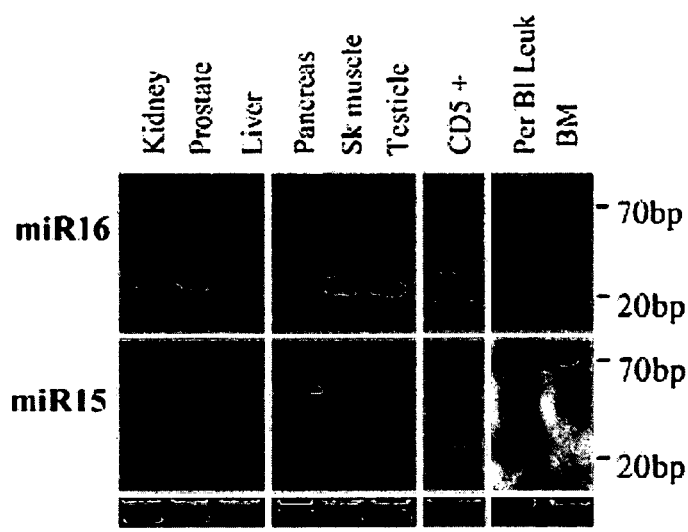
FIG. 3A is a Northern blot analysis of miR15 and miR16 gene expression in normal human kidney, prostate, liver, skeletal muscle ("Sk muscle"), testicle, CD5+ B cells (CD5+), leukemia cells ("Per B1 Leuk"), and bone marrow ("BM").

The miR15 and miR16 Genes are Localized in the Minimally Deleted Region of Chromosome 13 and are Highly Expressed in CD5+ Cells Publicly available sequence information and databases were screened for new regulatory genes in the minimal region of loss at 13q14. A cluster of two recently cloned miRNA genes, miR15 and miR16, were located exactly in the deleted region (FIG. 2A). To evaluate the level of expression of miR15 and miR16 in normal tissues, Northern blot analysis of miR15 and miR16 RNA was performed on a panel of normal-tissues, including CD5+ B cells isolated from tonsils of normal individuals (FIG. 3A). CD5+ B cells were used as controls, because B-CLL is characterized by a progressive accumulation of CD5+ B-lymphocytes. Ubiquitous expression of both miR15 and miR16 genes was found, with the highest level in normal CD5+ lymphocytes. In addition, miR16 was consistently expressed at higher levels than. miR15 in normal tissues. These data indicated that the miR15 and miR16 genes play an important role in normal CD5+ B-cell homeostasis.

Example 3

The miR15 and miR16 Genes are Frequently Deleted or Downregulated in CLL Samples with Deletions at 13q14

To investigate whether the miR15 and miR16 genes were involved in CLL pathogenesis, 60 CLL samples and 30 human cancer cell lines were analyzed for miR15 and miR16 expression by Northern blotting (FIG. 3A). 68% of CLL patients (41/60), as well as 5 out of 6 analyzed prostate cancer cell lines, showed a significant reduction in expression when compared with their normal tissue counterparts. These findings demonstrated that the miR15 and miR16 genes are down-regulated in the majority of B-CLL and prostate cancer cases tested.

In addition, 23 out of 60 CLL samples (38%) presented a clearly identifiable band of about 70 nt representing the miR15 precursor RNA. The 70 nt miR15 band was not found in any normal tissue analyzed except for bone marrow (FIG. 3A), which indicated that miR15 precursor RNA could be inefficiently processed in CLL.

Figure 3B:
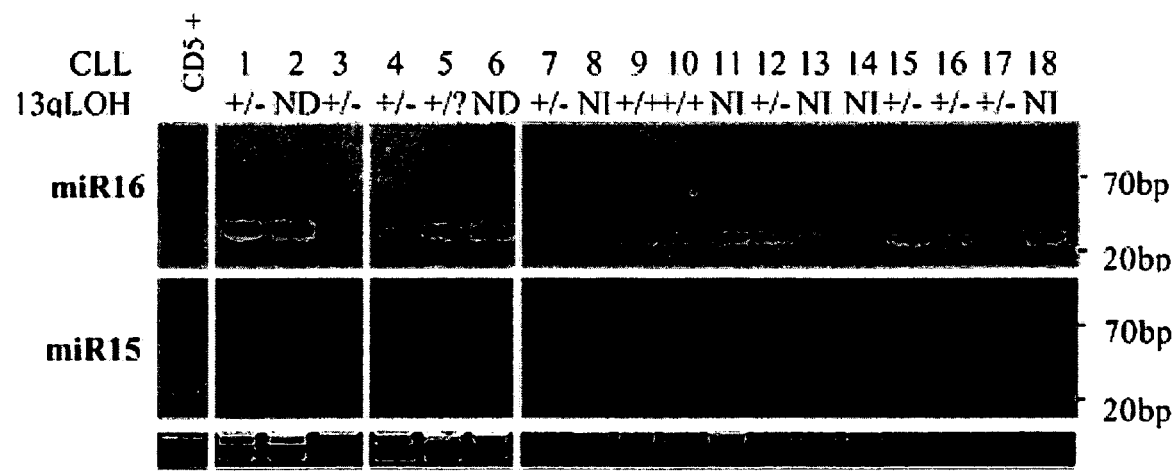
FIG. 3B is a loss of heterozygosity ("LOH") analysis of microsatellite makers D13S272 and D13S273 in 18 CLL patients. DNA from normal human CD5+ cells was used as a control. The LOH status for the samples is shown as "+/+ heterozygosity," "+/− LOH," "−/− homozygous deletion," "NI" (not informative), "?" (not enough material) and "ND" (not done). Ethidium bromide-stained Northern gels were used as normalization controls.

To determine whether the observed down-regulation of expression correlated with allelic loss in CLL, LOH studies were performed with microsatellite makers D13S272 and D13S273 on 46 CLL patients from whom normal DNA was available (FIG. 3B). We found that 68% of informative samples displayed LOH in at least one marker (24 out of 35 cases). In all but four samples (75%), expression of the miR15/16 gene products was reduced. For 12 samples, reproducible results were not obtained due to the poor quality of the starting material. Additionally, expression levels were reduced in 6 out of 11 cases (55%) without apparent LOH. In these cases, deletions may have been too small to be detected with the markers analyzed.

Northern blot analysis indicated that both miR15 and miR16 gene products were expressed in cases with known large homozygous deletions at 13q14 and with less than 5% normal cells, pointing to the presence of other highly similar micro RNA genes in the genome. Indeed, a cluster very similar to miR15/miR16 gene cluster (but with different precursors) has been reported on chromosome 3q25-26.1 (see Lagos-Quintana et al. (2002), *Curr. Biol.* 12:735-739). To show that the variation in miR15/16 gene expression was strictly related to deletions on chromosome 13q, probes specific for miR16 precursor RNA on chromosome 13 and for the miRNA precursor RNA produced from the gene on chromosome 3 were designed and used to probe Northern blots. While the miR16 precursor RNA from chromosome 13 was detected at low levels, no specific hybridization with the chromosome 3 probe was found in the same samples. In addition, an LOH study was performed with two microsatellite markers spanning a region of 2 Mb located immediately centromeric to this cluster. Four of 17 informative samples showed LOH in at least one marker, and no correlation with the levels of expression of miR15/16 was found. These data clearly demonstrated that down-regulation of miR15 and miR16 gene expression in CLL correlates with allelic loss at 13q14, and indicated a role for miR15 and miR16 gene products in CLL pathogenesis.

Example 4 miR15 and miR16 are also Involved in CLL Pathogenesis in Mice

To further investigate whether the miR15 and miR16 genes were involved in CLL pathogenesis, studies were extended to Eµ-TCL1 transgenic mice which develop CLL (Bichi et al., (2002), *Proc. Natl. Acad. Sci. USA* 99:10:6955-6960). Cytogenetic and genetic alterations were examined in Eµ-TCL1 transgenic mice. Northern blot analyses were performed as described above (see Examples—"Northern blotting," and Example 3).

In approximately 80% of the transgenic mice, there was a knock down of the mouse homologues of miR15 and miR16 in CLL cells, compared to normal mouse spleen lymphocytes. These results are similar to those described in Example 3 for human CLLs compared to normal human cells.

Comparisons were made between mouse chromosome 15 and human chromosome 12. Comparative gene hybridization (CGH) of the transgenic mouse leukemias showed that approximately 35% had an amplification of a region of mouse chromosome 15, which corresponds to a region of human chromosome 12. Cytogenetic analyses of these mouse leukemias also showed trisomies or tetrasomies of mouse chromosome 15. Trisomies of chromosome 12 are known to occur in approximately 25% of human CLLs.

Comparative gene hybridization also showed a loss of a region of mouse chromosome 14 (51.6-78.5 Mb) which corresponds to region 13q14 in humans.

The results of the studies indicate that the CLL mouse model recapitulates events occurring in the pathogenesis of human CLL. Taken together, the data presented in Examples 1-4 indicate a role for miR15 and miR16 in CLL pathogenesis in mammals.

Example 5

Analysis of Mutations did not Reveal Point Mutations in miR15 and miR16 Genes in CLL and Gastrointestinal Cancers In order to further evaluate involvement of the miR15 and miR16 genes in CLL, a set of 120 B-CLLs and 80 colorectal and gastric cancers were screened for mutations by direct sequencing of PCR amplification products. A 720 bp genomic region containing the entire cluster was amplified. In three cases, the same alteration was found in the miR16 precursor RNA; a T to C substitution at position 2. This change was not predicted to alter the hairpin structure of the miRNA. Several extragenic polymorphisms were also found. The paucity of mutations in the miR16 gene was not surprising given the small size (70 bp) of the miR16 gene.

In order to identify alternative mechanisms for inactivation of the remaining allele in CLL cases showing LOH, "in silico" cloning was used to identify a putative promoter region located about 215. bp downstream of the miR16 gene. Down regulation by promoter hypermethylation was reported for several cancer related genes including $p16^{INK4a}$, p73, hMLH1, or VHL (see Esteller (2002), *Oncogene* 21:5427-5440). Methylation-specific PCR was therefore used to analyze the methylation status of one CpG rich region located 5' from the putative miR16 promoter. There was no detectable difference in the methylation patterns in any of the analyzed CpG sites independent of the levels of miR15 or miR16 gene expression in ten CLL samples (eight with decreased expression and two with high expression). However, methylation of different regions or of small regions of CpG sites which escaped detection by the methylation-specific PCR cannot be excluded.

Example 6

Expression of miR15 and miR16 Gene Products in Human Cells

The cDNA sequences encoding the entire 70 nucleotide miR15 and miR16 RNA precursors are separately cloned into the context of an irrelevant mRNA expressed under the control of the cytomegalovirus immediate early (CMV-IE) promoter, according to the procedure of Zeng et al. (2002), *Mol. Cell* 9:1327-1333, the entire disclosure of which is herein incorporated by reference.

Briefly, Xho I linkers are placed on the end of double-stranded cDNA sequences encoding the miR15 and miR16 RNA precursors, and these constructs are separately cloned into the Xho I site present in the pBC12/CMV plasmid. The pBC12/CMV plasmid is described in Cullen, (1986), *Cell* 46: 973-982, the entire disclosure of which is herein incorporated by reference. The plasmid containing the miR15 precursor RNA sequences is called pCMV-miR15, and the plasmid containing the miR16 precursor RNA sequences is called pCMV-miR16.

pCMV-miR15 and pCMV-miR16 are separately transfected into cultured human 293T cells by standard techniques using the FuGene 6 reagent (Roche). Total RNA is extracted as described above, and the presence of processed miR15 or miR16 RNA is detected by Northern blot analysis with miR15 and miR16 specific probes.

pCMV-miR15 and pCMV-miR16 are also separately transfected into cultured human prostate carcinoma cell lines 2220, 2221, 11609, 11611, LNCAP, TSUR. Total RNA is extracted as described above, and the presence of processed miR15 or miR16 RNA in the prostate carcinoma cells is detected by Northern blot analysis with miR15 and miR16 specific probes. The transfected prostate carcinoma cells are also evaluated for changes in morphology, the ability to overcome contact inhibition, and other markers indicative of a transformed phenotype.

Example 7

Transfection of CLL Cells with miR15 and miR16 Gene Products

CLL cells from a subject diagnosed with CLL are isolated and transfected with plasmids encoding miR15 and miR16 micro RNAs as follows.

CD5+ B cells are isolated as described above and CLL cells are identified by visual inspection or by determining the CLL Score according to the scoring system of Matutes et al. (1994), *Leukemia* 8(10):1640-1645, the entire disclosure of which is herein incorporated by reference. CD5+ B cells with a CLL Score of at least 4 are considered CLL cells. Deletions in the 13q14 region which remove the miR15/miR16 gene cluster are confirmed in the isolated CLL cells.

The isolated CLL cells are transfected with pCMV-miR15 and pCMV-miR16 by standard techniques. Total RNA is extracted as described above, and the presence of processed miR15 or miR16 RNA detected by Northern blot analysis with miR15 and miR16 specific probes. Stable integration of miR15 and miR16 gene sequences is also confirmed by Southern blot hybridization using probes specific for miR15 and miR16 gene sequences.

Example 8

Transfection of Hematopoietic Stem Cells with miR15 and miR16 Gene Products

Hematopoietic stem cells (HSC) from subjects diagnosed with CLL are obtained from bone marrow as follows.

Bone marrow is harvested from the iliac bones of a subject under general anesthesia in an operating room using standard techniques. Multiple aspirations are taken into heparinized syringes for a total of about 750 to 1000 ml bone marrow. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) to obtain the "buffy coat" (i.e., leukocytes devoid of red cells and platelets).

The buffy coat preparation is partially enriched for hematopoietic stem cells (HSC) by positively selecting for $CD34^+$ cells with immunomagnetic beads (Dynal A. S., Oslo, Norway) as follows. The buffy coat preparation is suspended in supplemented alpha medium and incubated with mouse anti- HPCA-1 antibody in 1:20 dilution, 45 minutes, at 4° C. with gentle inverting of tubes. The cells are washed 3× in supplemented alpha medium, and then incubated with beads coated with the Fc fragment of goat anti-mouse IgG$_1$ (75 µl of immunobeads/$10^7$ CD34$^+$ cells). After 45 minutes of incubation at 4° C., cells adherent to the beads are positively selected using a magnetic particle concentrator, as directed by the manufacturer.

$2×10^4$ cells from the preparation enriched for HSC are incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer, and are transfected with pCMV-miR15 and pCMV-miR16 by standard techniques. Expression of miR15 or miR16 RNA is confirmed in a portion of the transfected HSC by Northern blot analysis, and stable integration of miR15 or miR16 gene sequences in a portion of the HSC is confirmed by Southern blot analysis. Approximately $4×10^8$/kg body weight to about $8×10^8$/kg body weight of the remaining transfected cells are reimplanted into the subject according to standard bone marrow transplant techniques.

The experiment is repeated, but the bone marrow is purged of neoplastic cells with ionizing radiation prior to transfection and reimplantation, as follows. Cells in the buffy coat preparation are adjusted to a cell concentration of about $2×10^7$/ml in TC-199 containing about 20% autologous plasma. Recombinant human hematopoietic growth factors rH IL-3 or rH GM-CSF are added to the cell suspension to stimulate growth of hematopoietic neoplasms and thereby increase their sensitivity to ionizing radiation. The cells are then exposed to 5-10 Gy ionizing radiation, washed once at 4° C. in TC-199 containing about 20% autologous plasma, and transfected with pCMV-miR15 and pCMV-miR16 as above.

Example 9

Preparation of Liposomes Encapsulating miR15 or miR16

Liposome Preparation 1—Liposomes composed of lactosyl cerebroside, phosphatidylglycerol, phosphatidylcholine and cholesterol in molar ratios of 1:1:4:5 are prepared by the reverse phase evaporation method described in U.S. Pat. No. 4,235,871, the entire disclosure of which is herein incorporated by reference. The liposomes are prepared in an aqueous solution of 100 µg/ml processed miR15 or miR16 RNA or 500 µg/ml pCMV-miR15 or pCMV-miR16. The liposomes thus prepared encapsulate either the processed miR15 or miR16 RNA, or the pCMV-miR15 or pCMV-miR16 plasmids.

The liposomes are then passed through a 0.4 polycarbonate membrane and suspended in saline, and are separated from non-encapsulated material by column chromatography in 135 mM sodium chloride, 10 mM sodium phosphate pH 7.4. The liposomes are used without further modification, or are modified as described below.

A quantity of the liposomes prepared above are charged to an appropriate reaction vessel to which is added, with stirring, a solution of 20 mM sodium metaperiodate, 135 mM sodium chloride and 10 mM sodium phosphate (pH 7.4). The resulting mixture is allowed to stand in darkness for 90 minutes at a temperature of about 20° C. Excess periodate is removed by dialysis of the reaction mixture against 250 ml of buffered saline (135 mM sodium chloride, 10 mM sodium phosphate, pH 7.4) for 2 hours. The product is a liposome having a surface modified by oxidation of carbohydrate hydroxyl groups to aldehyde groups. Targeting groups or opsonization inhibiting moieties are conjugated to the liposome surface via these aldehyde groups.

Liposome Preparation 2—A second liposome preparation composed of maleimidobenzoyl-phosphatidylethanolamine (MBPE), phosphatidylcholine and cholesterol is obtained as follows. MBPE is an activated phospholipid for coupling sulfhydryl-containing compounds, including proteins, to the liposomes.

Dimyristoylphosphatidylethanolamine (DMPE) (100 mmoles) is dissolved in 5 ml of anhydrous methanol containing 2 equivalents of triethylamine and 50 mg of m-maleimidobenzoyl N-hydroxysuccinimide ester, as described in Kitagawa et al. (1976), *J. Biochem.* 79:233-236, the entire disclosure of which is herein incorporated by reference. The resulting reaction is allowed to proceed under a nitrogen gas atmosphere overnight at room temperature, and is subjected to thin layer chromatography on Silica gel H in chloroform/methanol/water (65/25/4), which reveals quantitative conversion of the DMPE to a faster migrating product. Methanol is removed under reduced pressure and the products re-dissolved in chloroform. The chloroform phase is extracted twice with 1% sodium chloride and the maleimidobenzoyl-phosphatidylethanolamine (MBPE) purified by silicic acid chromatography with chloroform/methanol (4/1) as the solvent. Following purification, thin-layer chromatography indicates a single phosphate containing spot that is ninhydrin negative.

Liposomes are prepared with MBPE, phosphatidylcholine and cholesterol in molar ratios of 1:9:8 by the reverse phase evaporation method of U.S. Pat. No. 4,235,871, supra, in an aqueous solution of 100 µg/ml processed miR15 or miR16 RNA or a solution of 500 µg/ml pCMV-miR15 or pCMV-miR16. Liposomes are separated from non-encapsulated material by column chromatography in 100 mM sodium chloride-2 mM sodium phosphate (pH 6.0).

Example 10

Attachment of Anti-CD5+ or Anti-Prostate Tumor Antibodies to Liposomes Encapsulating miR15 or miR16

An appropriate vessel is charged with 1.1 ml (containing about 10 mmoles) of Liposome Preparation 1 carrying reactive aldehyde groups, or Liposome Preparation 2 above. 0.2 ml of a 200 mM sodium cyanoborohydride solution and 1.0 ml of a 3 mg/ml solution of a monoclonal antibody directed against the CD5+ cell surface marker or a prostate tumor cell antigen is added to the preparation, with stirring. The resulting reaction mixture is allowed to stand overnight while maintained at a temperature of 4° C. The reaction mixture is separated on a Biogel A5M agarose column (Biorad, Richmond, Calif.; 1.5×37 cm).

Example 11

Inhibition of Human Prostate Tumor Growth in Vivo with miR15 or miR16 Gene Products A hormone refractory human prostate adenocarcinoma cell line (PC-3) is inoculated into nude mice, and the mice are divided into treatment and control groups. When tumors in the mice reach 100 to 250 cubic millimeters, processed miR15 and miR16 encapsulated in liposomes are injected directly into the tumors of the control group. The tumors of the control, group are injected with liposomes encapsulating carrier solution only. Tumor volume is measured throughout the study. The efficacy of miR15 and miR16 gene products to inhibit prostate tumor growth in the Dunning R-3327 rat prostate adenocarcinoma model is also evaluated, as follows. A highly metastatic and malignant clone (RT-3.1) of Dunning R-3327 prostate adenocarcinoma cells is inoculated into Copenhagen rats, which are then divided into treatment and control groups. Both groups form solid tumor masses in approximately one week. The tumors of rats in the treatment group are then injected with processed miR15 and miR16 encapsulated in liposomes twice a week for 5 weeks. The tumors of the control group are injected with liposomes encapsulating carrier solution only. Tumor volume is measured throughout the study.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

---

What is claimed is:

1. A method of diagnosing an miR15-mediated B-cell chronic lymphocytic leukemia in a subject, comprising the step of measuring the level of an miR15 gene product that comprises a nucleotide sequence selected from the group consisting of SEQ ID NO:1 and SEQ ID NO:3 in a sample containing chronic lymphocytic leukemia B-lymphocytes obtained from the subject, wherein a lower level of the miR15 gene product in the sample, relative to a control miR15 gene product sample, indicates that the subject has a miR15-mediated B-cell chronic lymphocytic leukemia.

2. The method of claim 1, wherein the level of the miR15 gene product is measured using an assay selected from the group consisting of northern blot analysis, in situ hybridization, and quantitative reverse transcriptase polymerase chain reaction.

3. The method of claim 1, wherein the sample is a tissue sample.

4. The method of claim 3, wherein the tissue sample is selected from the group consisting of a biopsy sample and a blood sample.

5. The method of claim 1, wherein the sample is a fluid sample.

6. A method of diagnosing an miR15-mediated prostate cancer in a subject, comprising the step of measuring the level of an miR15 gene product that comprises a nucleotide sequence selected from the group consisting of SEQ ID NO:1 and SEQ ID NO:3 in a sample containing prostate cancer cells obtained from the subject, wherein a lower level of the miR15 gene product in the sample, relative to a control miR15 gene product sample, indicates that the subject has a miR15-mediated prostate cancer.

7. The method of claim 6, wherein the level of the miR15 gene product is measured using an assay selected from the group consisting of northern blot analysis, in situ hybridization, and quantitative reverse transcriptase polymerase chain reaction.

8. The method of claim 6, wherein the sample is a tissue sample.

9. The method of claim 8, wherein the tissue sample is selected from the group consisting of a biopsy sample and a blood sample.

10. The method of claim 6, wherein the sample is a fluid sample.

* * * * *

UNITED STATES PATENT AND TRADEMARK OFFICE
CERTIFICATE OF CORRECTION

PATENT NO. : 7,723,035 B2
APPLICATION NO. : 11/375650
DATED : May 25, 2010
INVENTOR(S) : Carlo Croce and George Calin Page 1 of 1

It is certified that error appears in the above-identified patent and that said Letters Patent is hereby corrected as shown below:

In the Specification

In Column 1, Line 16, replace:
"The invention described herein was supported in part by grant nos. P01CA76259, P01CA81534, and P30CA56036 from the National Cancer Institute."

With:
--This invention was made with government support under CA056036, CA081534, and CA076259 awarded by the National Institutes of Health.--

Signed and Sealed this
Tenth Day of June, 2025

Coke Morgan Stewart
*Acting Director of the United States Patent and Trademark Office*